US 8,840,382 B2

(12) United States Patent
Al-Harbi

(10) Patent No.: US 8,840,382 B2
(45) Date of Patent: Sep. 23, 2014

(54) BLOOD-PUMPING DEVICE

(75) Inventor: Abdulrahman Futayn Al-Harbi, Tabuk (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 13/344,445

(22) Filed: Jan. 5, 2012

(65) Prior Publication Data

US 2012/0171063 A1 Jul. 5, 2012

Related U.S. Application Data

(63) Continuation of application No. PCT/EP2010/004124, filed on Jul. 6, 2010.

(30) Foreign Application Priority Data

Jul. 6, 2009 (SA) .............................. SA109300439

(51) Int. Cl.
*F04B 43/12* (2006.01)
*F04B 45/08* (2006.01)

(52) U.S. Cl.
CPC ............. *F04B 43/12* (2013.01); *F04B 43/1284* (2013.01); *F04B 43/1253* (2013.01); *F04B 43/1238* (2013.01)
USPC .................................................. 417/477.11

(58) Field of Classification Search
CPC .. F04B 43/12; F04B 43/1284; F04B 43/1253; F04B 43/1238
USPC ................ 417/474, 476, 477.3, 477.6, 477.7, 417/477.8, 477.9, 477.11; 604/6.09
See application file for complete search history.

(56) References Cited

U.S. PATENT DOCUMENTS 2,988,001 A * 6/1961 Arcey et al. .................... 417/429
3,421,447 A * 1/1969 Jackson ...................... 417/477.6
(Continued)

FOREIGN PATENT DOCUMENTS

| EP | 0269898 A3 | 6/1988 |
| GB | 2152241 B | 7/1985 |
| SA | 109300439 | 7/2009 |
| WO | WO0035513 | 6/2000 |

OTHER PUBLICATIONS

PCT Search Report for PCT Application No. PCT/EP2010/004124, mailed Oct. 20, 2010 (13 pages).

(Continued)

*Primary Examiner* — Bryan Lettman
(74) *Attorney, Agent, or Firm* — Lee & Hayes, PLLC; Benjamin A. Keim

(57) ABSTRACT

A blood-pumping device comprises a cavity with a U-shaped wall comprising two straight regions connected by an arch-shaped region and a U-shaped tube aligned with the U-shaped wall of the cavity to provide a support for the U-shaped tube, wherein the U-shaped tube comprises two straight regions connected by a semicircular region. The blood-pumping device further comprises an arm rotatable about a center point of the semicircular region, wherein the arm holds two wheels a distance from each other such that upon rotation of the arm the wheels roll along the U-shaped tube while putting pressure on the U-shaped tube, wherein the arch-shaped region of the U-shaped wall of the cavity comprises a recessed portion so that the wheels of the arm impose less pressure on the tube at the recessed portion and upon rotation of the arm generates a pulsating blood flow.

14 Claims, 3 Drawing Sheets

(56) References Cited

U.S. PATENT DOCUMENTS

| | | | | |
|---|---|---|---|---|
| 3,963,023 | A | * | 6/1976 | Hankinson ..................... 604/19 |
| 5,626,563 | A | | 5/1997 | Dodge et al. |
| 2006/0067845 | A1 | * | 3/2006 | Kojima et al. ................ 417/476 |
| 2007/0296744 | A1 | * | 12/2007 | Kubota et al. ..................... 347/7 |

OTHER PUBLICATIONS

Austrialian Office Action dated Jun. 5, 2013, Appln No. 2010270547, a counterpart foreign application of U.S. Appl. No. 13/344,445, 4 pgs.

* cited by examiner

BLOOD-PUMPING DEVICE

CROSS REFERENCE TO RELATED APPLICATIONS

This application is a 35 U.S.C. 371 National Stage Application of International Application No. PCT/EP2010/004124, filed Jul. 6, 2010, which claims priority to Saudi Arabian Patent Application SA109300439, filed Jul. 6, 2009, the entire contents of which both are incorporated herein by reference.

FIELD OF THE INVENTION

The present invention relates to a blood-pumping device and in particular to a Cardio-Pulmonary bypass device used in heart surgery for providing an artificial heart.

BACKGROUND OF THE INVENTION

During heart surgery blood that under normal conditions is pumped by the heart is during surgery streamed out of the body to a pumping device (pumping machine), which is configured to provide a blood circulation in the human body that is normally provided by the natural heart. The artificial heart has to maintain the blood flow during the surgery until the natural heart can be re-activated after the end of the surgery.

The heart pulse is deactivated during a heart surgery and the natural heart has completely stopped to pump blood so that the physician can perform the surgical work. As the human body, however, needs the blood to stay alive, the blood is circulated by an external blood pumping device to provide a blood circulation through the body and the blood-pumping device has to perform the functions of the natural heart. In order to provide a pulsatile blood flow existing systems aim to mimic the natural blood flow. However, these systems do not provide the natural pulsating behavior of the heart. For example, one available solution changes the blood streaming from a continuous (non-pulsating) mode to a pulsating mode by controlling the pumping speed, for example, by alternating between a fast and a slow pumping speed. These systems mimic the natural blood pulsing in the body during surgery, but do not provide a real pulse wave. A further disadvantage of these systems is that they need to change permanently the pumping speed (e.g. the rotation velocity of a pumping engine) and thus these systems do not work in a constant operational mode so that the wear and tear of these devices is increased.

Therefore, there is a need for a blood-pumping device providing a pulsating blood flow which comes as close as possible to the natural pulsating blood flow while operating in a constant operational mode. The object of the present invention is therefore to provide a blood-pumping device generating a pulsating blood flow by simple means.

SUMMARY OF THE INVENTION

In accordance with the present invention, a blood-pumping device according to claim 1 solves the above-said problems. Claims 2 to 7 provide particular advantageous realizations of the pumping device of claim 1. The invention also covers a Cardio-Pulmonary bypass device according to claim 8.

The blood-pumping device according to the present invention comprises a cavity with an at least partly U-shaped wall, the at least partly U-shaped wall comprising at least two straight regions and a arch-shaped (or curved) region connecting the two straight regions as well as a U-shaped (or curved) tube of deformable material, which is at least partially aligned with the at least partly U-shaped wall of the cavity to provide a support for the U-shaped tube, wherein the U-shaped tube comprises a first and a second straight regions connected by a semicircular region or a region essentially in the form of a segment of a circle. The blood-pumping device further comprises an arm rotatable about a center point of the semicircular region, wherein the arm holds a first and a second wheel in a distance from each other such that upon rotation of the arm the wheels roll along the U-shaped tube while putting pressure on the U-shaped tube. The arch-shaped region of the U-shaped wall of the cavity comprises a recess portion so that the wheels of the arm impose less pressure on the tube at the recess portion than on the tube outside the recess portion and upon rotation of the arm a pulsating blood flow is generated. Thus, the pulsating blood flow is generated by a decreasing pressure imposed by the wheels when entering the recessed portion and an increasing pressure when the wheels leave the recessed portion.

In further embodiments the arm comprises a first arm with the first wheel and second arm with the second wheel such that the arms are mounted with one end on an engine head and the first and second wheels are mounted at an end that is opposite to the one end of the arms. The blood pumping device may also comprise a blank space formed opposite to the recess portion of the U-shaped wall along which the tube does not extend. In further embodiments the recess portion comprises a movable alignment piece, which is movable in the direction away from the center point or is optionally be formed with a depth profile adapted to a desired pressure profile of the blood flow. The alignment piece may also comprise an indicator for indicating the distance between the alignment piece and the tube. The blood-pumping device may further comprise a control unit being configured to adjust the rotational velocity of the arm to mimic a natural heart pulse. Further embodiments relate also to a Cardio-pulmonary bypass device including said blood-pumping device.

BRIEF DESCRIPTION OF THE DRAWINGS

The present invention will become apparent from the following detailed description and the attached drawings in which.

DETAILED DESCRIPTION

Figure 1:
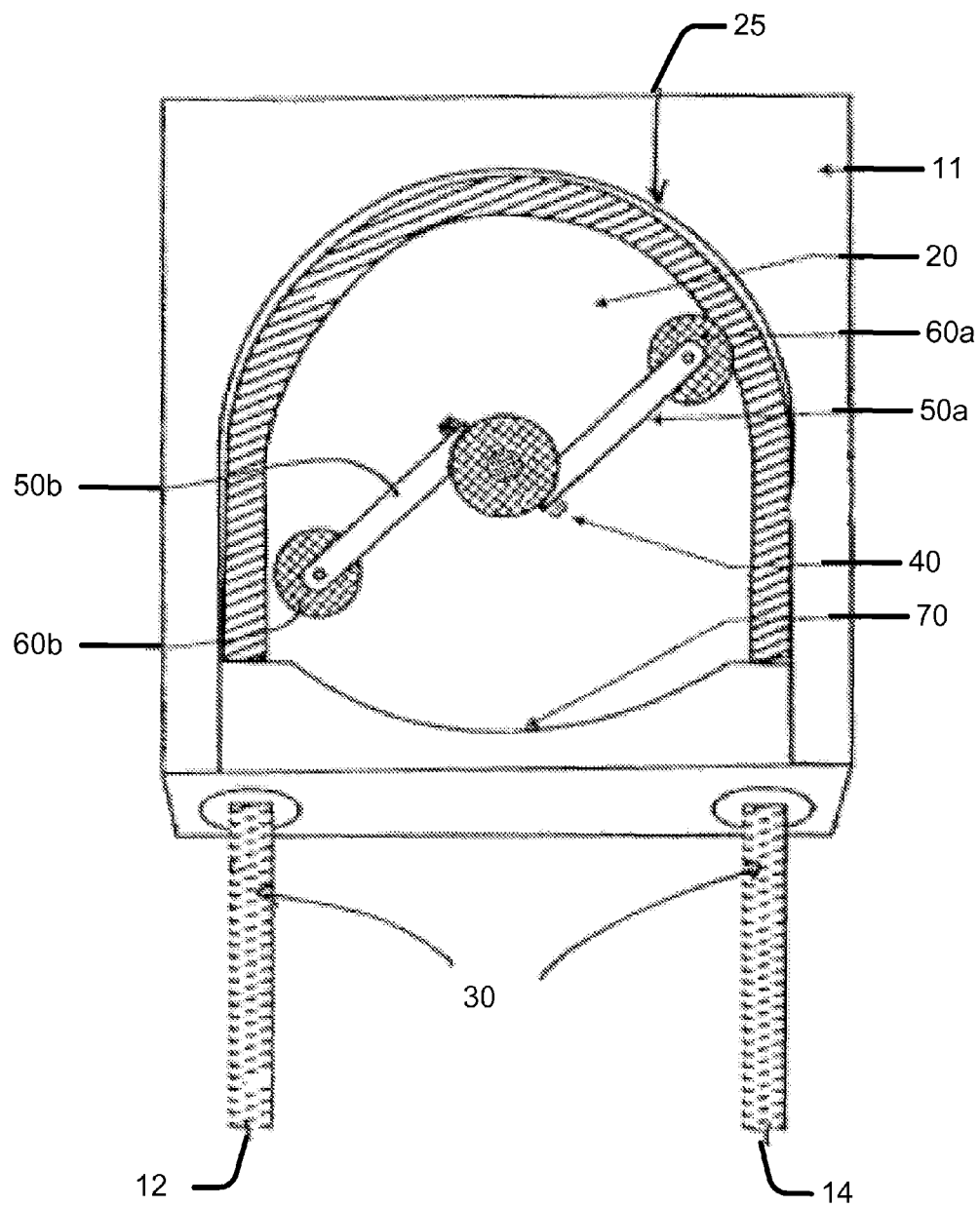
FIG. 1 shows a conventional blood-pumping device.

FIG. 1 shows a head of a conventional blood pump providing non-pulsating blood flow during a heart surgical operation, wherein pulsating blood flow can be generated only by changing the speed of the pumping engine. The shown blood pump comprises a pump head 11 with a cavity 20 (vacuum space) comprising an inverted U-shape with a semicircular portion 25 and an opposite blank space 70. A tube 30 with an inlet 12 and an outlet 14 is provided for carrying the blood coming from the body via the inlet 12 passing the cavity 20 and returning back to the human body via the outlet 14. The tube 30 comprises also a U-shape such that it is supported by the U-shaped cavity 20, which provides also a backing for the tube 30. The tube 30 extends not along the blank space 70, but only along the U-shape part of the internal wall of the cavity 20.

An engine of the pump (not shown in the figure) rotates an engine head 40 around a middle point M (center point) of the semicircular part of the U-shaped tube 30. At the engine head two extended arms 50a, 50b are mounted such that upon rotation of the engine both arms 50a, 50b circulate about the center point M. Each arm 50a, 50b comprises a wheel 60a, 60b at its end portions away from the center point M such that the wheels 60 put a pressure on the tube 30 while rotating the engine head 40 together with the arms 50a, 50b, because the tube 30 is backed by the internal wall of the cavity 20. Thus, the tube 30 is placed in-between the wheels 60 on one hand and the internal vacuum wall 20 on the other hand and is made of deformable material (e.g. a rubber material) to deform under the pressure imposed by the wheels 60. By rotating the engine head 40 the two arms are circulating and thereby putting pressure on the tube 30, which varies with the rotation along the tube 30 to pump the blood from the inlet 12 (from the body) to the outlet 14 (to the body).

The blood pump as shown in FIG. 1 leads therefore to a constant non-pulsating flow of blood, because at any time at least one of the two wheels 60a, 60b is in contact with the tube 30, thereby deforming the tube and pushing the blood inside the tube 30 towards the outlet 14 of the pump 11. Because the tube 30 extends only along the U-shape shape of the cavity, but does not pass through the blank space 70 of the inverted U-shape as shown in FIG. 1, this blank space 70 does not affect the constant non-pulsating blood flow. If the first wheel 60a is inside this blank space 70, the second wheel 60b continues to deform the tube 30 and hence generating pressure on the blood contained in the tube 30 and, therewith, transporting the blood towards the outlet 14.

Hence, the blood pump as shown in FIG. 1 can generate a pulsating blood flow only by modulating the speed of the engine head 40 to alternate between a slow and fast moving stage (i.e. the angular velocity of the rotating arms about the center point M varies). Therefore, only by changing the operation mode a blood flow that mimics a pulsating flow during the surgery can be provided by the system according to FIG. 1.

The present invention provides a new solution to achieve a pulsating blood provided to a body during a surgery, without interfering in the speed of the pumping engine.

Figure 2:
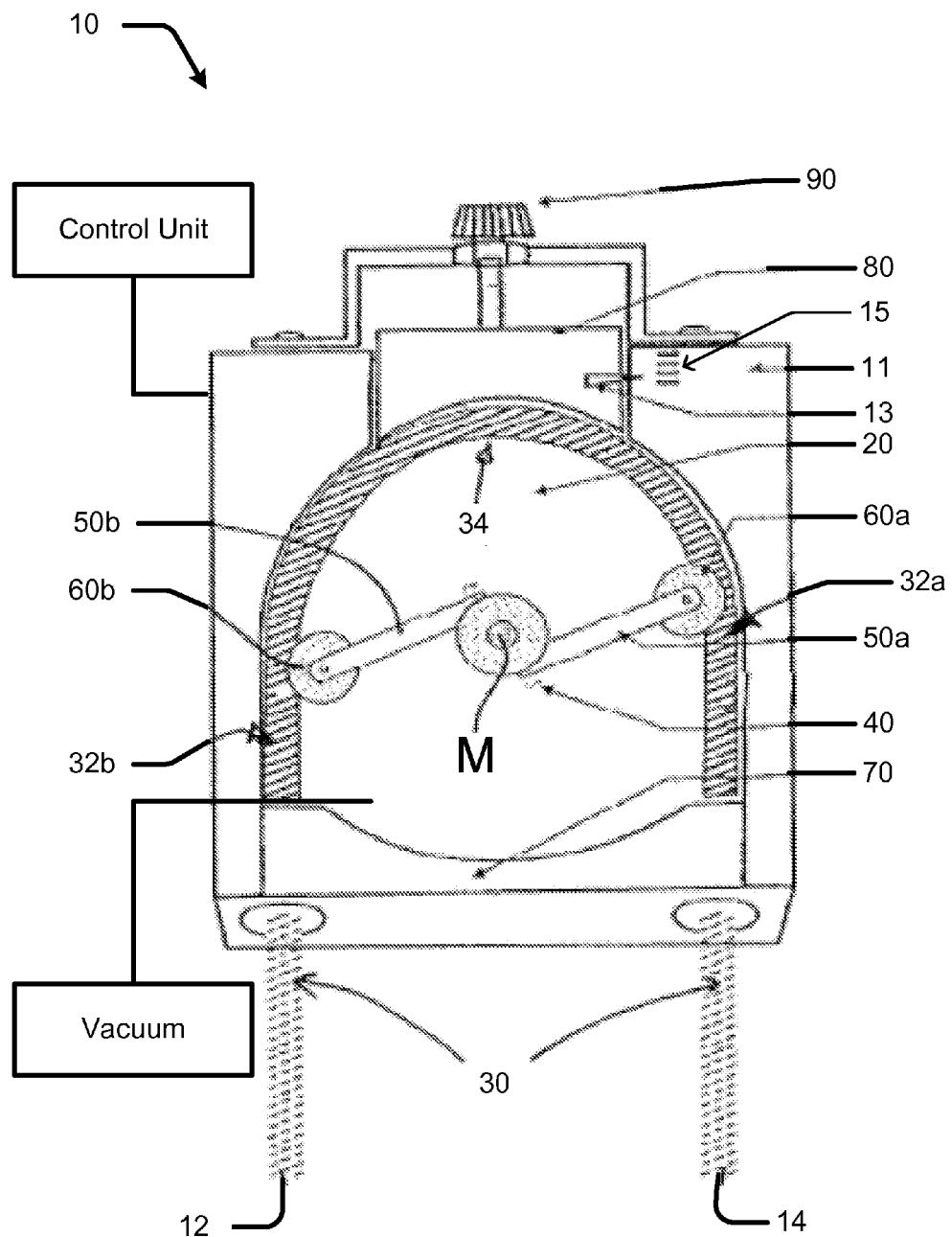
FIG. 2 shows a blood-pumping device according to the present invention in closed position generating a continuous blood flow.

FIG. 2 shows a head of a blood pump according to an embodiment of the present invention usable during the heart surgical operation, wherein a movable, adjustable component (alignment piece) is at a closed position generating constant non-pulsating blood flow in the same way as the device of FIG. 1. If the adjustable component is in the open position, a pulsating flow is generated as will be described in FIG. 3 The device of FIG. 2 has many features in common with the device of FIG. 1 so that a repeated description of common components can be avoided here.

The blood-pumping device as shown in FIG. 2 again comprises a cavity 20 with a U-shaped internal wall comprising two straight regions and a arch-shaped region connecting the two straight regions. The arch-shaped region comprises at least partially a semicircular portion 25 as in FIG. 1. The blood-pumping device 10 comprises also a U-shaped tube 30 comprising a first and a second straight region 32a and 32b connected by a semicircular region 34. As in FIG. 1 the tube 30 is at least partially aligned with the U-shaped internal wall of the cavity 20 to provide a support (i.e. a backing) for the U-shaped tube 30 so that the tube 30 passes only along the U-shape of the cavity 20, but is formed at the blank space 70 of the inverted U-shape.

Moreover, the pumping device of FIG. 2 comprises also an arm 50 mounted rotatably about a central point M of the semicircular region 34 of the tube 30, wherein the arm 50 holds a first and a second wheel 60a, 60b in a distance from each other such that upon rotation of the arm 50 the wheels 60 roll along the U-shapes tube while providing a pressure on the U-shaped tube. The pumping device 10 comprises also a blood inlet 12 and a blood outlet 14 such that upon a clockwise rotation of the arm 50 about the central point M blood is carried from the inlet 12 to the outlet 14. Because at any time at least one of the two wheels 60 are in contact with the tube 30, thereby deforming the tube 30, the rolling wheels 60 push and pull blood in a clockwise direction around the semicircular part 34 of the tube 30 and a constant (non-pulsating) flow is generated. In a further embodiment a counter-clockwise rotation of the arm 50 is used to operate the pump in a reverse direction, i.e. pumping blood from the outlet 14 to the inlet 12. Optionally, the arm 50 may again comprise a first and a second arm 50a, 50b as described in FIG. 1.

In contrast to the blood pumping device as shown in FIG. 1, the blood-pumping device 10 of FIG. 2 comprises an alignment piece 80, which is movable and is adjusted to provide a semicircular inner wall of the U-shaped internal wall of the cavity 20 so that the tube 30 is in contact to the alignment piece 80 when the wheels 60 roll over the tube 30 on the side opposite to the alignment piece 80 and thus generating pressure within the tube 30.

Figure 3:
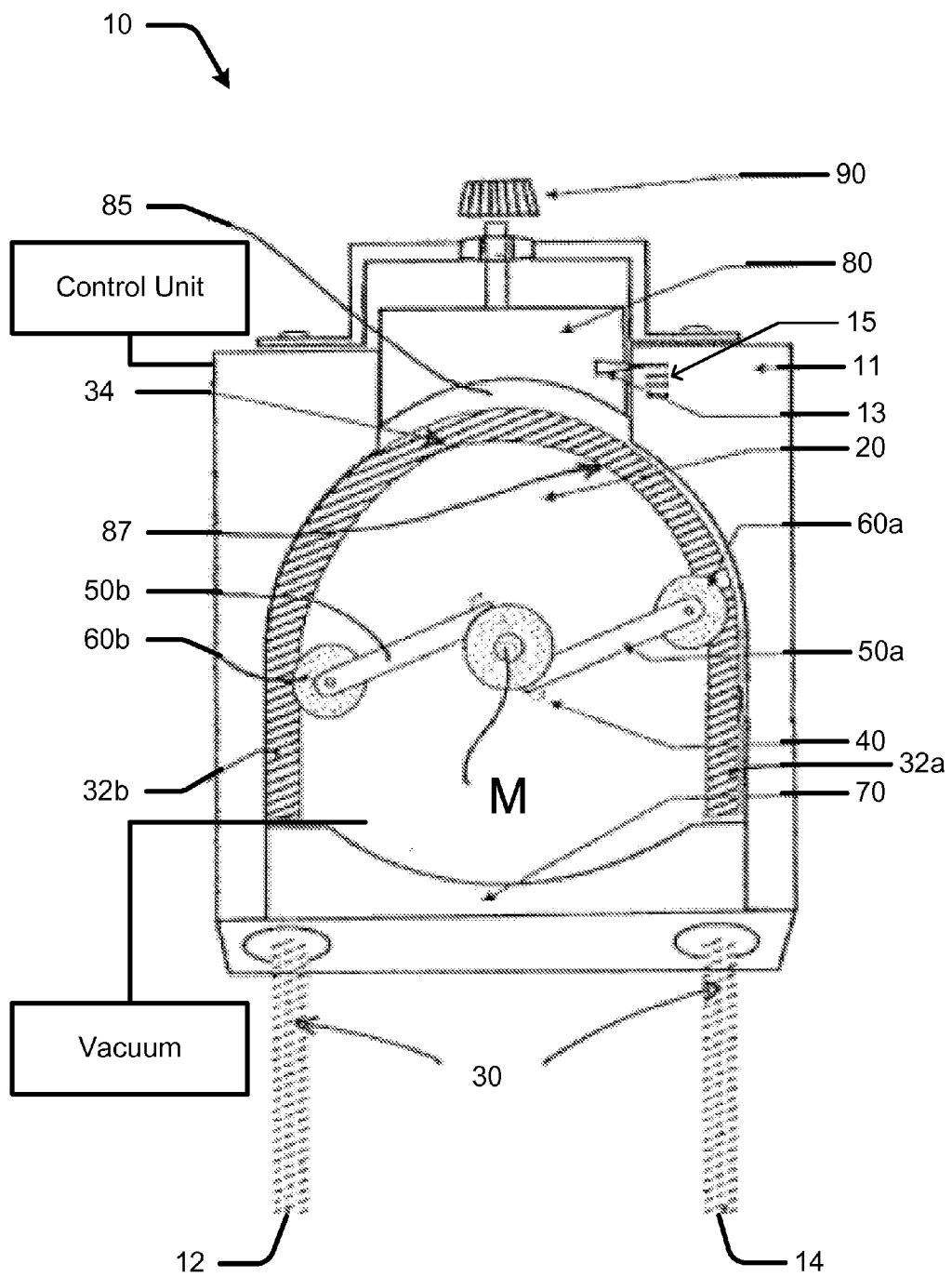
FIG. 3 shows the blood-pumping device of FIG. 2 in an open position generating an intervallic pulsating blood flow.

FIG. 3 shows the same head of the blood pump (blood-pumping device 10) as in FIG. 2, but wherein the movable alignment piece 80 is moved into an open position providing an intervallic pulsating blood flow used during heart surgical operations.

In comparison to the blood-pumping device of FIG. 2, the alignment piece 80 is moved in a direction away from the center point M so that between the alignment piece 80 and the tube 30 an open space 85 appears and, in contrast to the situation as shown in FIG. 2, the tube 30 is not supported anymore by the alignment piece 80. Therefore, when the wheels 60 roll on the tube 30 and reach the position of the open space 85, the wheels 60 do not deform the tube 30 at this position and hence the pressure inside the tube 30 is also relaxed. In particular, if for example the second wheel 60b reaches the position opposite to the alignment piece 80 the first wheel 60a is in region of the blank space 70 so that also the first wheel 60a does not provide pressure on the tube 30. As consequence, when the second wheel 60b passes the open space 85 and the first wheel 60a passes the blank space 70 the blood pressure is relaxed. When the second wheel 60b reaches again the point 87, where the tube 30 is supported by the U-shaped internal wall of the cavities 20, the tube 30 will again deform and the blood pressure increases again generating a pulsating blood flow. Thus, the rotating arm 50 generates alternating high and low pressure phases in the flow (pulsating blood flow) by alternating between a low pressure state when one of the wheel 60 is at the alignment piece 80 (or at the open space 85) and a high pressure state when the one wheel 60 is outside the alignment piece 80.

Therefore, embodiments of the present invention use two techniques. In addition to the engine head as shown in FIG. 1 the alignment piece 80 is added in the arch-shaped part of the cavity 20 opposite to the empty U-shaped blank space 70, which is movable to be out of contact with the tube 30. An aligning knob or handle can be used to move up and down the alignment piece 80 and by adjusting the alignment piece 80 away from the aligned position (where the inner wall aligns to form a semicircular shape), the blood pressure in the tube 30 decreases when wheels 60 simultaneously pass both, the blank space 70 and the free space 85 (low pressure phase of the pulsating blood flow). This arrangement provides the advantage that a desired pulse frequency can easily be adjusted by the angular velocity of the arm(s) 50 (pulse frequency is twice the number of revolutions per minute, because each revolution generates two beats of the artificial heart).

In further embodiments, the alignment piece 80 may be provided with an indicator 13 for indicating graduations 15 of distance from the original position, which can be used during operation to further improve the resulting blood pressure power. For example, when the alignment piece 80 is very close to the tube 30 the difference between the low pressure and the high pressure phases of the pulsating blood is be very low, whereas with increasing distance of the alignment piece from the tube 30 the difference between the low pressure and high pressure phases of the blood increases.

Furthermore, upon revolving the engine head 40 the two arms 50 circulate around the center point M and the two connected wheels 60 put pressure on the blood tube 30, which is supported by the internal wall of the cavity 20. Hence, the blood is pulled inside the cavity 20 from the blood inlet 12 and pushed outside from the blood outlet 14 towards the body during the surgery. When the wheels 60 pass the blank space 70 the pressure is weakened, because the other wheel is moving into the region of the alignment piece 80 (open space 85), whereby the pulsating pressure is mimicked.

In further embodiments in the cavity 20 a vacuum is established improving the relaxation of the tube 30 after rolling over with the wheels 60 (because the blood pressure inside the tube 30 can more easily expand the tube 30 if a vacuum is outside the tube 30). In further embodiments the alignment piece 80 is replaced by a recessed region in the wall, which may be not movable too. The recessed region can be formed with a (depth) profile to generate a desired pressure profile of the blood flow.

Therefore, embodiments of the present invention provide a solution to achieve a pulsating flow of blood from and to a body during surgery without interfering with the rotation speed in the pumping engine. This effect is achieved by providing two portions (two vacuum spaces), wherein the wheels do not put pressure on the tube thereby releasing for a time period the pressure on the blood inside the tube. The two vacuum spaces (open space 85 and blank space 70) for the circulating arm 50 facing each other in the blood-rotation head and make the blood pumping weak upon reaching said spaces and get stronger again upon leaving said vacuum spaces.

Hence, embodiments provide an external blood-pumping head used in blood-pumping systems during surgeries. It contains an inverted U-shape with a rotating head in the middle, with two arms extended from the head. The arms barely touch the vacuum wall internally. The blood tube passes adjacent to the mentioned vacuum wall, between the vacuum wall and the arms. The arms put pressure on the tube to push up the blood inside the tube from the human body and re-pump it back during the rotation of the arms. The mentioned vacuum wall has two vacuums opposing each other; one of these vacuums has a moving, tightening wall integrating the shape of the internal circle. It can be pulled out to reduce the blood pressure during pumping the blood back to the body. This generates a similar mimic of the natural heart pulses by moving the alignment head and the two arms in circles inside the mentioned vacuum. Further embodiments provide an external blood pumping head used in blood pumping systems during surgeries. As said in the previous embodiment, the mentioned alignment wall can be adjusted in different grades.

The invention claimed is:

1. A blood-pumping device, comprising:
a cavity with an at least partly U-shaped wall, the at least partly U-shaped wall comprises two straight regions and an arch-shaped region connecting the two straight regions;
a U-shaped tube of a deformable material for carrying blood, which is at least partially aligned with the at least partly U-shaped wall of the cavity to provide a support for the U-shaped tube, wherein the U-shaped tube comprises a first and a second straight region connected by a semicircular region; and
an arm being rotatable about a center point of the semicircular region, wherein the arm holds a first and a second wheel in a distance from each other such that upon rotation of the arm the wheels roll along the U-shaped tube thereby exerting a pressure on the U-shaped tube,
wherein the arch-shaped region of the U-shaped wall of the cavity comprises a recess portion, wherein the recess portion has a depth profile adapted to a desired pressure profile of the blood flow and comprises a movable alignment piece, which is movable in a direction away from the center point, and wherein said arch-shaped region and said recess portion are arranged such that the pressure exerted by one of the wheels at the recess portion is less than the pressure exerted by the one wheel on the U-shaped tube at the arch-shaped region at a position outside said recess portion, thereby generating a pulsating blood flow inside the U-shaped tube upon rotation of the arm, wherein the moveable alignment piece comprises an indicator for indicating gradations of distance between an original position of the moveable alignment piece and the U-shaped tube.

2. The blood-pumping device of claim 1, wherein the arm comprises a first arm with the first wheel and a second arm with the second wheel such that the first and second arms are mounted with one end on an engine head and the first and second wheels are mounted at an end opposite to the one end of the first and second arms.

3. The blood-pumping device of claim 2, further comprising a blank space formed opposite to the recess portion of the U-shaped wall, wherein the tube is not formed in the blank space.

4. The blood-pumping device of claim 2, further comprising a control unit being configured to adjust a rotational velocity of the arm to mimic a natural heart pulse.

5. The blood-pumping device of claim 1, further comprising a blank space formed opposite to the recess portion of the U-shaped wall, wherein the tube is not formed in the blank space.

6. The blood-pumping device of claim 1, further comprising a control unit being configured to adjust a rotational velocity of the arm to mimic a natural heart pulse.

7. A Cardio-Pulmonary bypass device including the blood-pumping device according to claim 1.

8. The blood-pumping device of claim 1, wherein a vacuum is established in the cavity thereby improving relaxation of the U-shaped tube after rolling over with the first and second wheels.

9. The blood-pumping device of claim 1, wherein movement of the moveable alignment piece towards the center point decreases a pressure difference between alternating high and low pressure phases of the pulsating blood flow and movement of the moveable alignment piece away from the center point increases the pressure difference between alternating high and low pressure phases of the pulsating blood flow.

10. A device, comprising:
a cavity with an at least partly U-shaped wall, the at least partly U-shaped wall comprises two straight regions and an arch-shaped region connecting the two straight regions, wherein the cavity is configured to hold a tube of a deformable material;
an arm being rotatable about a center point of the semicircular region, wherein the arm holds a plurality of wheels in a distance from each other, individual ones of the plurality of wheels configured to exert a pressure on the tube at the arch-shaped region;
wherein the arch-shaped region comprises a recess portion, having a depth profile adapted to a desired pressure phase profile of fluid flowing through the tube due to a pressure exerted on the tube by individual ones of the plurality of wheels at the recess portion being less than the pressure exerted by individual ones of the plurality of wheels at a portion of the arch-shaped region outside the recess portion; and
a movable alignment piece, forming at least a portion of the arch-shaped region, which is movable both towards and away from the center point thereby adjusting the depth profile of the recess portion; and
a knob or handle configured to control movement of the moveable alignment piece towards and away from the center point, the knob or handle positioned on a housing of the device such that the moveable alignment piece is between the center point and the knob or handle.

11. The device of claim 10, further comprising a control unit being configured to adjust the rotational velocity of the arm to mimic a natural heart pulse.

12. A Cardio-Pulmonary bypass device including the device according to claim 10.

13. The device of claim 10, wherein a vacuum is established in the cavity thereby improving relaxation of the tube after rolling over with the plurality of wheels.

14. The device of claim 10, wherein the moveable alignment piece comprises an indicator for indicating gradations of distance between an original position of the alignment piece and the tube.

* * * * *